(12) United States Patent
Randel

(10) Patent No.: US 11,464,819 B2
(45) Date of Patent: *Oct. 11, 2022

(54) CANNABINOIDS INFUSED CONSUMABLES AND NON-CONSUMABLES

(71) Applicant: Michael William Randel, Lakebay, WA (US)

(72) Inventor: Michael William Randel, Lakebay, WA (US)

(*) Notice: Subject to any disclaimer, the term of this patent is extended or adjusted under 35 U.S.C. 154(b) by 209 days.

This patent is subject to a terminal disclaimer.

(21) Appl. No.: 17/039,829

(22) Filed: Sep. 30, 2020

(65) Prior Publication Data

US 2022/0096582 A1   Mar. 31, 2022

(51) Int. Cl.
  *A61K 36/00* (2006.01)
  *A61K 36/185* (2006.01)
  *A61K 47/44* (2017.01)
  *A61K 47/46* (2006.01)

(52) U.S. Cl.
  CPC ............ *A61K 36/185* (2013.01); *A61K 47/44* (2013.01); *A61K 47/46* (2013.01); *A61K 2236/31* (2013.01); *A61K 2236/37* (2013.01)

(58) Field of Classification Search
  None
  See application file for complete search history.

(56) References Cited

U.S. PATENT DOCUMENTS

| | | |
|---|---|---|
| 10,028,987 B1 | 7/2018 | Pillsbury |
| 10,103,225 B2 | 10/2018 | Reillo et al. |
| 2017/0196923 A1 | 7/2017 | Moore |
| 2018/0200315 A1 | 7/2018 | Silver |

FOREIGN PATENT DOCUMENTS

| | | |
|---|---|---|
| CA | 2859930 A1 | 3/2016 |

*Primary Examiner* — Michael V Meller
(74) *Attorney, Agent, or Firm* — Thomas LaGrandeur

(57) ABSTRACT

The present disclosure is directed to cannabinoids infused consumables and non-consumables and methods of producing the cannabinoid infused consumables and non-consumables. The consumables are infused in an overall two-step process, in which cannabinoids from a *Cannabis* species are first infused into coconut oil, which in turn is used to infuse a food or beverage of choice with cannabinoids to generate the cannabinoids infused consumables. The non-consumables are produced by adding a cannabinoids infused oil to the non-consumables.

10 Claims, 3 Drawing Sheets

CANNABINOIDS INFUSED CONSUMABLES AND NON-CONSUMABLES

FIELD OF THE INVENTION

The invention relates to whole cannabis infused coconut oil which in turn is used to infuse a variety of consumables and non-consumables.

BACKGROUND

*Cannabis* has been used to alleviate stress and other illnesses caused by posttraumatic stress disorder, seizures, epilepsy, multiple sclerosis, and the like. *Cannabis*, commonly known as marijuana or hemp, is a genus of flowering plants that includes at least three species, *Cannabis sativa, Cannabis indica*, and *Cannabis ruderalis*.

*Cannabis* plants produce a variety of potentially useful or beneficial cannabinoids, which produce mental and physical effects when consumed. Cannabinoids are a chemical group or family of 21-carbon-containing terpenophenolic compounds produced by *Cannabis* species. Current estimates of the number of cannabinoids found in *Cannabis* species is well in excess of 100 different cannabinoids. Two of the most prominent cannabinoids are Cannabidiol (CBD) and Tetrahydrocannabinol (THC). In addition to CBD and THC, other cannabinoids such as cannabichromene (CBC), cannabigerol (CBG), cannabinol (CBN), and others are present in varying amounts in cannabis plant material.

Commonly consumed sources of cannabinoids include extracts, oils, isolates, and the like from *Cannabis* species including marijuana, hemp, and industrial hemp, which contains a THC content of less than 0.3% of overall mass. While providing useful or beneficial effects to the user, such extracts, oils, and isolates are typically found to have undesirable tastes, flavors, odors, and/or other unfavorable attributes. Accordingly, addition of cannabinoid containing extracts or isolates to food or beverage consumables imparts an undesirable taste, since the extracts or isolates typically have an undesirable taste.

Accordingly, there exists a need in the art for consumable cannabinoid-containing consumables that do not have the tastes and odors of typically consumed sources of cannabinoid. The presently disclosed cannabinoid-containing consumables along with methods of preparing such consumables address this need. In addition, the presently disclosed methods can be used in the preparation of non-consumable products.

SUMMARY

The present disclosure provides for orally ingestible, cannabinoid infused consumables and methods of producing such.

The method disclosed entails an overall two-step process in which coconut oil or other food grade oil is first infused with cannabinoids from a species of *Cannabis*. In the second step, the cannabinoid infused coconut oil is used to infuse a given consumable to generate a cannabinoid infused food consumable. A cannabinoid infused food consumable, such as cocoa beans, can be used to generate a cannabinoid infused beverage, such as hot chocolate.

An overall preferred embodiment of generating cannabinoid infused consumables is presented herein. As detailed below, the method involves a series of steps of heating and cooling/freezing consumables in the presence of a source of cannabinoids (either *Cannabis* buds or coconut oil) to produce a cannabinoid infused consumable.

In a preferred embodiment, a method of infusing oil for use in non-consumable products is disclosed.

The presently disclosed cannabinoid infused consumables are more fully described in the detailed description below.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF EXEMPLARY EMBODIMENTS

As is known in the art, cannabinoid is a class of chemical compounds found in plants in the cannabis family (e.g., hemp, marijuana, etc.). To date, at least 113 cannabinoids have been identified, accounting for up to 40% of the plant's extract. Well known cannabinoids include Cannabidiol (CBD), Tetrahydrocannabinol (THC) among others, each of which may include a variety of health benefits.

In general, the presently disclosed cannabinoids infused consumables relate to a wide variety of foods and, in some cases, resultant beverages made from the food/consumable that provide a source cannabinoids. The presently disclosed consumables are infused with cannabinoids in a way that increases the levels and quantities of cannabinoids transferred to the consumables while reducing undesirable tastes, flavors, odors and the like typically associated with and found in commonly used cannabinoid extracts, oils, isolates, edibles and such.

As used herein, the term "infused cannabinoids" or "cannabinoid infused" refers to various foods and/or drinks to which cannabinoids have been infused by a method(s) disclosed herein. The infusion method generally involves preparing a mixture made with whole cannabis plant materials and coconut oil (or similar oil) under specific heating and cooling conditions, and then in turn using the infused oil mixture to infuse consumables as detailed herein. Throughout this specification, cannabinoid infused food and/or drink may be referred to as "cannabinoid infused" or simply "infused," such as "cannabinoid infused cocoa beans" or "infused cocoa beans."

Figure 1:
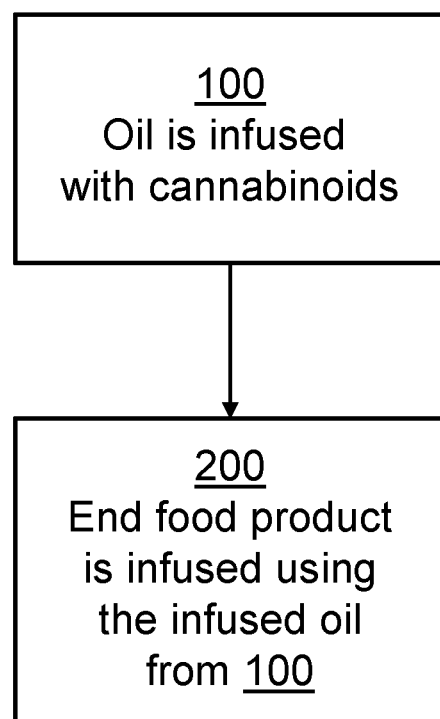
FIG. 1 shows example steps of a method according to exemplary embodiments hereof.

In some embodiments as shown in FIG. 1, cannabinoid infused foods and/or drinks prepared by the methodology disclosed herein are generated in an overall two-step process. In the first step (at 100), whole cannabis plant material is ground or used whole and used to infuse an oil, such as coconut oil, with cannabinoids. Note that because whole cannabis plant material is used at 100, the resulting mixture may be referred to as a full spectrum cannabis and oil mixture. In a second step (at 200), the infused coconut oil is used to infuse an end food product/consumable with cannabinoids. After the end product is infused with cannabinoids, it may be consumed in any typical fashion, such as direct consumption, used to make a beverage as in the case of cocoa beans, and so forth.

Consumption of the cannabinoid food and drink consumables generated by the methods described herein provides the beneficial effects generally associated with cannabinoids. These effects include, but are not limited to, mental and physical effects, such as pain relief from CBDs and other cannabinoids, mental high from THC (in foods infused with marijuana cannabinoids), and other effects attributed to consumption of cannabinoids.

Figure 2:
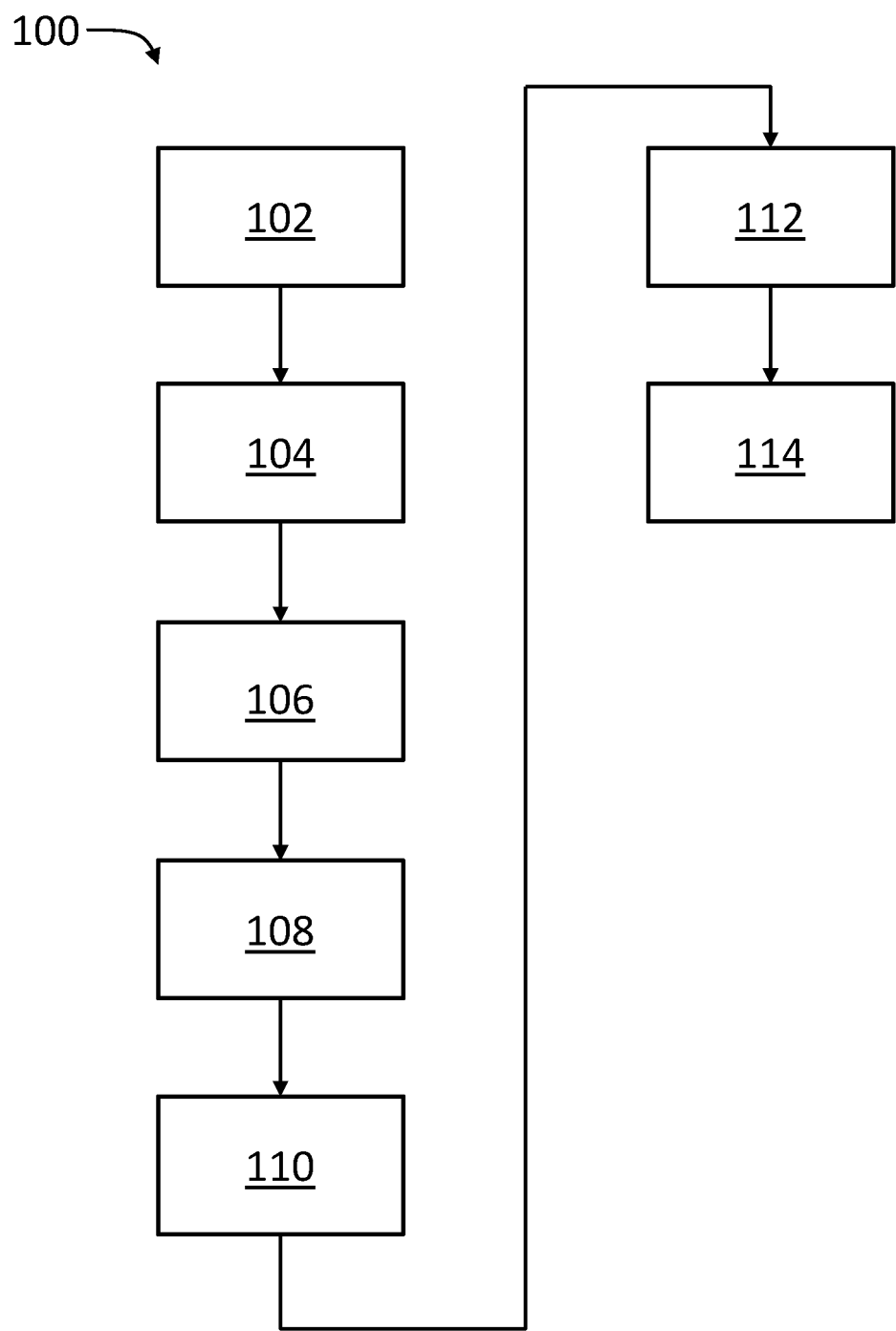
FIG. 2 shows example steps of a method according to exemplary embodiments hereof.

FIG. 2 refers to steps that may be taken to infuse a food grade oil with cannabinoids to complete step 100 of FIG. 1. Suitable food grade oils for this process include, but are not limited to, coconut oil, MCT oil (medium chain triglycerides oil), vegetable oil, sunflower oil, grape seed oil, and combinations thereof. Likewise, butter, shortening, margarine, or lard may be used in the process.

In one embodiment as shown in FIG. 2, whole, raw cannabis plant material (e.g., flowers, buds, leaves or other plant material; preferably buds) is frozen, preferably for 24 hours (at 102). The cannabis plant material can be used whole or ground (which is preferably produced by grinding the frozen plant material). The cannabis plant may include *Cannabis Sativa, Cannabis Indica, Cannabis Ruderalis*, other types of cannabis and any combination thereof. The cannabis may be classified as marijuana, hemp, and/or other types of cannabis.

Next (at 104), a suitable food grade oil such coconut oil, MCT oil, a combination of coconut oil and MCT oil (or similar oil as described above) is heated to a temperature equal to or between 150° and 200° F., and preferably to about 175° F. For the purposes of this specification, the term "about" used in relation to temperatures will mean within ±1%. Regarding a combination of coconut oil and MCT oil, a preferred embodiment is to use a ratio of 75% coconut oil to 25% MCT oil.

Next (at 106), the cannabis (preferably buds) is added to the coconut oil and held at the temperature (e.g., preferably at about 175° F.) for 4-8 hours (preferably 8 hours), while occasionally (and/or continuously) stirring the mixture. In some embodiments, the ratio of plant material to coconut oil is 1 lb plant material to 2 gallons oil. For example, on a commercial scale, 100 lbs plant material/buds may be mixed with 200 gallons of oil. However, other ratios within 10%, 20%, 30%, 40%, 50%, 75%, 100% of this ratio also may be used. In general, the ratio will be chosen to provide the desired concentration(s) of cannabinoids within the oil.

After this (at 108), the cannabis and coconut oil mixture is frozen for 8-12 hours, and preferably for about 12 hours.

Then (at 110), the cannabis and coconut oil mixture is reheated to 150° to 200° F., and preferably to about 175° F., and held at the temperature for a sufficient period of time to liquify the mixture, typically for about 2-4 hours.

Next (at 112), the cannabis and coconut mixture is strained using a press bag (or other suitable straining techniques) and the strained material is separated.

In a further step (114), the strained, cannabinoid infused oil is heated to 250° F. for 2 hours. This step will decarboxylate the carboxylated cannabinoids in the oil, such as CBD-A or THC-A. As noted below, this step can be removed/not utilized when it is desirable to have carboxylated cannabinoids, such as CBD-A in the oil. It can be desirable to have such an infused oil for use in non-consumable products, such as hair care products.

This method results in a in a cannabinoid infused oil mixture that may be used for direct consumption and/or for use in infusing other end products with cannabinoids as described below.

Figure 3:
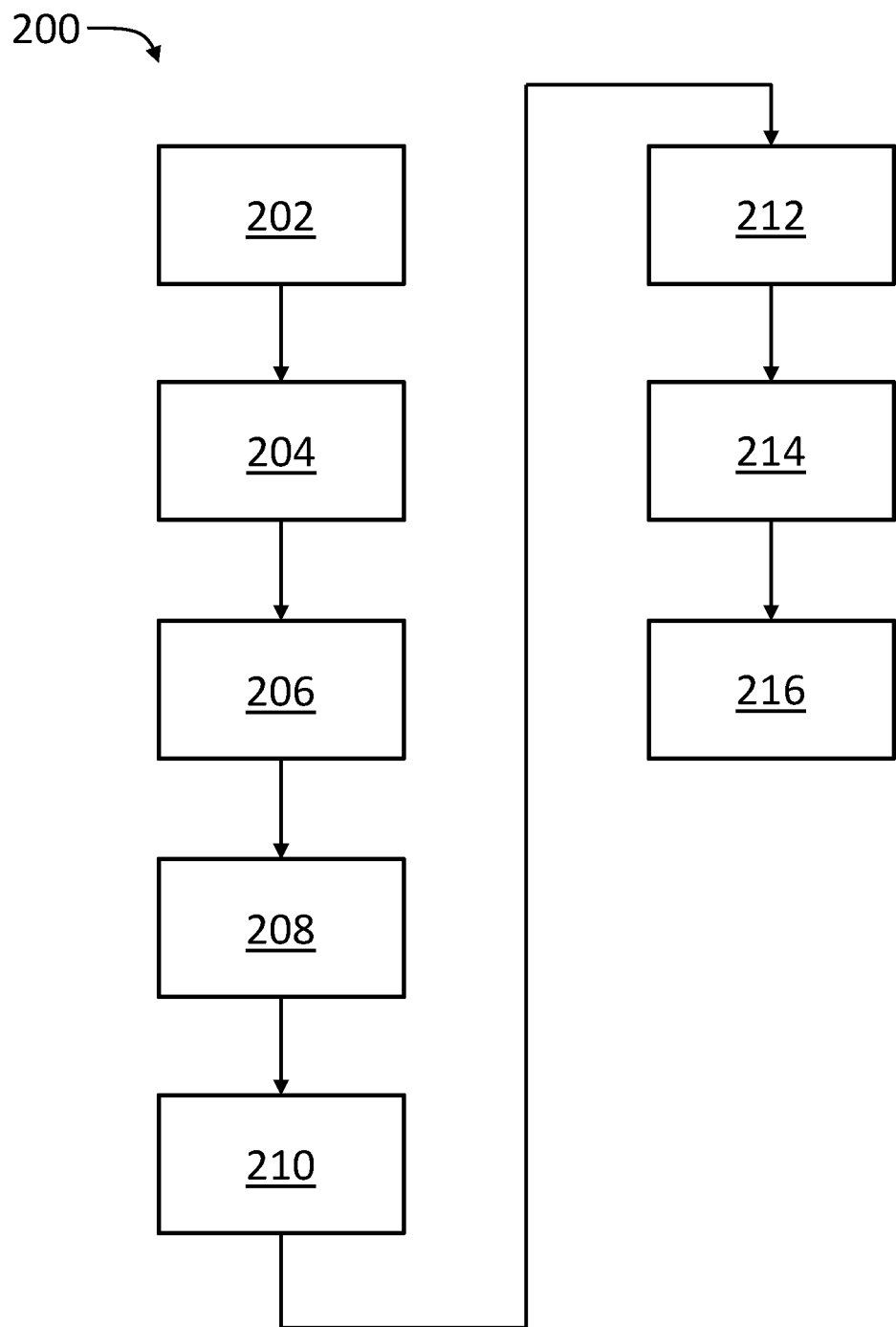
FIG. 3 shows example steps of a method according to exemplary embodiments hereof.

In another embodiment as shown in FIG. 3, a cannabis and coconut mixture, such as the mixture obtained from the process 102-114 (FIG. 2) described above, is used to infuse consumable products. Consumable products that may be infused include, but are not limited to, popcorn (microwave popcorn, kettle corn, caramel popcorn, popcorn with nuts, popcorn with nuts and caramel, and so forth), raw cocoa beans and resultant chocolate products (hot chocolate, chocolate bars, chocolate chips, chocolate bars with nuts and/or fruit, chocolate bars with nougat, and so forth), granola bars, granola bars with nuts and/or fruit, oatmeal with nuts and/or fruit, nut butters (peanut butter, almond butter, etc.), all food grade oils and butter (butter, margarine, medium chain triglycerides (MCT) oil, coconut oil, shortening, lard, vegetable oil, sunflower oil, olive oil, grape seed oil), flavored coconut oil (garlic, herbs, spices, bacon, fruit, nuts, coffee flavored oils and so forth), dehydrated fruits, fresh fruit, jams and jellies, canned fruit, frozen fruit, ice cream, baked goods (cookies, cookies with nuts and/or fruit, brownies, brownies with nuts and/or fruit), caramel sauce, and a variety of combinations thereof.

The method generally includes steps that include, but are not limited to, those described below. As described below, there are a variety of modifications to the general method depending on the consumable or type of consumable that is being infused with cannabinoids from infused coconut oil. Such modifications are presented in several of the Examples below.

First (at 202), at least a portion of the strained cannabis and coconut oil mixture obtained from 102-114 (FIG. 2) is heated to a first temperature (for example, between 175° F. and 185° F.).

Next (at 204), a selection of consumables is added and stirred into the mixture (preferably with continuous stirring) and held at the first temperature for a period of time (for example, about 175° F. to 185° F. for about 8-9 hours). For the purposes of this specification, the term "about" used in relation to periods of time will mean ±3%. Referring to a commercial scale as described above in, which 200 gallons of starting oil was mixed with 100 lbs of plant material, this step will occur in a 400 gallon stock pot.

Next (at 206), the mixture including the consumable(s) is frozen (for example, for about 8-10 hours). On a commercial scale, this step can be carried out by covering the 400 gallon stock pot with a freezer blanket that will rapidly freeze the mixture and keep it frozen. Alternatively, the material can be rapidly frozen in a blast freezer.

Then (at 208), the mixture including the coffee beans, nuts, seeds, etc., is heated to a second temperature for a period of time (for example, equal to or between 175° F. and 185° F. for about 8-9 hours).

Next (210), the mixture including the consumable(s) is frozen (for example, for about 8-10 hours, as described above for step 206).

Then (at 212), the mixture including the consumable(s) is heated to a third temperature equal to or between 100° F. and 150° F., and held at the third temperature for a sufficient period of time to liquify the oil, typically about 2-4 hours, and preferably for about 2 hours.

After this (at 214), the mixture is strained (using any suitable straining techniques) and the consumable(s) are removed.

Then (at 216), the consumable(s) can be frozen, such as in a blast freezer, and stored frozen for subsequent use/consumption. Alternatively, the consumable(s) are packaged or used for consumption, making various infused products, and so forth.

This process 202-216 (FIG. 3) results in a selection of consumables infused with cannabinoids thereby producing cannabinoid infused consumables.

In some embodiments, the freezing steps at 206 and/or at 210 provide organic pressure to the consumables that deepens the physical depth of the cannabinoid infusion into the consumables. For example, in some embodiments, the freezing steps at 206 and/or at 210 cause the cannabinoids to be pressed 10%, 20%, 30%, 40%, 50%, 60%, 70%, 80%, 90% and/or 100% to the center of each consumable.

It is understood that the acts described above are meant as a general overview and demonstration of an exemplary method, and that the method may include different and/or additional acts as described herein or otherwise.

While the present invention has been described as having particular configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

It is understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first," "second," and so on, in the description and claims, are used to distinguish or identify, and not to show a serial or numerical limitation. Similarly, letter labels (e.g., "(A)", "(B)", "(C)", and so on, or "(a)", "(b)", and so on) and/or numbers (e.g., "(i)", "(ii)", and so on) are used to assist in readability and to help distinguish and /or identify, and are not intended to be otherwise limiting or to impose or imply any serial or numerical limitations or orderings. Similarly, words such as "particular," "specific," "certain," and "given," in the description and claims, if used, are to distinguish or identify, and are not intended to be otherwise limiting.

As used herein, including in the claims, the terms "multiple" and "plurality" mean "two or more," and include the case of "two." Thus, e.g., the phrase "multiple ABCs," means "two or more ABCs," and includes "two ABCs." Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" or "approximately 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

While the invention has been described in connection with what is presently considered to be the most practical and preferred embodiments and is further described in the examples below, it is to be understood that the invention is not to be limited to the disclosed embodiment, but on the contrary, is intended to cover various modifications and equivalent arrangements included within the spirit and scope of the appended claims.

EXAMPLE I

Popcorn

Cannabinoids infused popcorn kernels may be made by infusing popcorn kernels with a cannabinoids infused oil. In the case of popcorn kernels, suitable infused oils include essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2.

To infuse popcorn kernels with cannabinoids from a cannabinoids infused oil, raw kernels are added to oil at a temperature between 150° F. and 200° F. (preferably 170° F.) for 4-8 hours. The kernels and oil mixture is then frozen for 6-12 hours. The frozen mixture is then heated to a temperature between about 100° F. and 150° F. to liquify the oil, which typically takes about 2 hours in the specified temperature range. Once the oil in the mixture is liquified, the cannabinoids infused kernels and oil are separated by an appropriate separation means, such as filtration through a nylon mesh filter. The infused kernels can then be used directly for popcorn or can be treated using methods that impart various flavors and/or seasoning to the popcorn. Infused kernels that are to be use directly for popcorn are typically stored in a cooking oil, typically at about a 1:1 kernels to oil ratio. The infused kernels can then be popped directly from the stored mixture.

EXAMPLE II

Cocoa Beans

Cannabinoids infused cocoa beans may be made by infusing cocoa beans with a cannabinoids infused oil, such as infused coconut oil or any of the other oils and combinations thereof disclosed herein. The process by which cocoa beans are infused with cannabinoids closely follows the general process described above and outlined in FIGS. 2 and 3. The heating steps described in the process 202-216 (FIG. 3) for infusing cocoa beans are typically carried out at a temperature between 150° F. and 200° F. (preferably 170° F.). Once the cannabinoids infused cocoa beans are obtained, they can be stored frozen to help preserve freshness and slow/prevent deterioration of the cannabinoids that reduces the efficacy of the cannabinoids.

The cannabinoids infused cocoa beans can be processed in any of a variety of methods similar to standard cocoa beans (which are not infused) to produce cannabinoid infused cocoa and chocolate products, such as but not limited to, hot chocolate beverage, chocolate chips, chocolate bars, chocolate bars with nuts and fruit, chocolate bars with nougat, and so on. In a preferred embodiment, cannabinoids infused chocolate bars with nuts and/or fruits are made with chocolate from cannabinoids infused cocoa beans and cannabinoids infused nuts and/or infused fruits that are produced by the methods disclosed herein. Such chocolate bars made with cannabinoids infused chocolate, nuts, and/or fruits have a greater level of cannabinoids and therefore potency than chocolate bars made solely with cannabinoids infused chocolate with nut and/or fruits that are not infused.

EXAMPLE III

Coffee Beans

Cannabinoids infused coffee beans may be made by infusing coffee beans with a cannabinoids infused oil, such as infused coconut oil. The process by which coffee beans are infused with cannabinoids closely follows the general process described above and outlined in FIGS. 2 and 3. The heating steps described in the process 202-216 (FIG. 3) for infusing coffee beans are typically carried out at a temperature between 175° F. and 185° F. Once the cannabinoids infused coffee beans are obtained, they can be stored frozen to help preserve freshness and slow/prevent deterioration of the cannabinoids that reduces the efficacy of the cannabinoids.

EXAMPLE IV

Granola Bars

Cannabinoids infused granola bars can be made using suitable cannabinoids infused oils that include essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2.

Once a suitable cannabinoids infused oil is produced, the infused oil can be used as an oil base for granola bars. The bars can be made with a variety of cannabinoids infused nuts and/or seeds that are formed into granola bars with oatmeal or a similar foodstuff that is commonly used in granola bars. Such granola bars formed in this manner can contain a significant amount of cannabinoids.

EXAMPLE V

Infused Raw Fruit

Cannabinoids infused fruit can be made using suitable cannabinoids infused oils that include essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2.

Once a suitable cannabinoids oil is produced, the infused oil can be used to infuse fruit with cannabinoids. In a preferred embodiment, infused MCT oil is used, given its relatively low melting/liquifying temperature. To infuse raw fruit, the raw fruit is mixed with the cannabinoids infused oil at a temperature between about 100° F. and 150° F. for 15 minutes to one hour. The mixture of infused oil and fruit is then frozen for 12 hours. Following the freezing, the mixture is liquified at a temperature between about 100° F. and 150° F. and then the fruit is separated from the oil using an acceptable straining method, such as straining through a nylon mesh filter. Preferably, the type of raw fruit used in this process has a relatively high density that helps keep the fruit intact throughout the process. For example, pineapple and mango are fruits that have been used in this process to produce cannabinoids infused pineapple and mango. The infused fruits can be stored frozen to help preserve the integrity of the cannabinoids. The fruits can be consumed directly or used in other foods, such as the aforementioned chocolate and granola bars.

EXAMPLE VI

Infused Dehydrated Fruit

Cannabinoids infused dehydrated fruit can be made using suitable cannabinoids infused oils that include essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2.

Once a suitable cannabinoids oil is produced, the infused oil can be used to infuse dehydrated fruit with cannabinoids. The process by which dehydrated fruit is infused with cannabinoids closely follows the general process described above and outlined in FIGS. 2 and 3. The heating steps described in the process 202-216 (FIG. 3) for infusing dehydrated fruit is typically carried out at a temperature between 175° F. and 185° F. Once the cannabinoids infused dehydrated fruit is obtained, the fruit can be stored frozen to help preserve freshness and slow/prevent deterioration of the cannabinoids that reduces the efficacy of the cannabinoids.

EXAMPLE VII

Infused Garlic and Beans

Cannabinoids infused garlic and beans (such as pinto beans, navy beans, and other similar beans) can be made using suitable cannabinoids infused oils that include essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2.

Once a suitable cannabinoids oil is produced, the infused oil can be used to infuse garlic or beans with cannabinoids. The process by which garlic or beans are infused with cannabinoids closely follows the general process described above and outlined in FIGS. 2 and 3. The heating steps described in the process 202-216 (FIG. 3) for infusing garlic and beans is typically carried out at a temperature between 150° F. and 170° F. for 3-4 hours. Once the cannabinoids infused garlic or beans are obtained, the garlic or beans can be stored frozen to help preserve freshness and slow/prevent deterioration of the cannabinoids that reduces the efficacy of the cannabinoids.

EXAMPLE VIII

Infused Bacon

Cannabinoids infused bacon can be made using suitable cannabinoids infused oils that include essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2.

Once a suitable cannabinoids oil is produced, the infused oil can be used to infuse bacon with cannabinoids. To infuse bacon, raw bacon is initially laid out on a baking pan or similar baking sheet that preferably has raised edges. The bacon is then coated with the cannabinoids infused oil, along with a sufficient amount of infused oil to keep a layer of infused oil in the bottom of the baking pan to ensure that the bacon is exposed to the infused oil. The bacon with infused oil is then frozen for 4-12 hours. After freezing, the bacon with infused oil is heated to a temperature between 170° F. and 250° F. for 2-4 hours or until the bacon is crisp. The resulting cannabinoids infused bacon is then strained from the cannabinoids infused oil and resulting cannabinoids infused bacon grease (such that there is a cannabinoids infused oil and bacon grease mixture). The bacon is then stored for subsequent use, preferably either frozen or at a refrigerated/cool temperature.

The resulting cannabinoids infused oil and bacon grease mixture is a bacon flavored mixture that can be used in the methods disclosed herein to infuse consumables with cannabinoids and impart/add a bacon flavor to the consumable. For example, the cannabinoids infused oil and bacon grease mixture can used to prepare popcorn as detailed above, resulting in a cannabinoids infused, bacon flavored popcorn.

EXAMPLE IX

Infused, Flavored Oil

As detailed above, cannabinoids infused food grade oils can be produced using essentially all food grade oils and butter, including but not limited to, coconut oil, butter, MCT oil, shortening, lard, vegetable oil, sunflower oil, olive oil, grape seed oil, and combinations thereof. Any of these oils and butter can be infused with cannabinoids using the oil infusion process described above and outlined in FIG. 2. Cannabinoids infused oils and butter can be used to infuse various consumables by the methods described above and outlined in FIG. 3 as well as the various specific examples described herein, such as those for infused raw fruit, bacon, garlic, and so on. The methods described herein may also be used to produce infused cooking flavoring agents, such as herbs and spices. Such cannabinoid infused, flavoring agents (herbs and spices) can be used on food to provide cannabinoids and flavor.

Once a cannabinoids consumable is produced by the methods described herein, the residual cannabinoids infused oil can typically be used in the process again since the residual infused oil still typically contains a significant amount of cannabinoids. In this manner, residual infused oil typically can be used in the process once or twice, such that infused oil can overall be used 2-3/several times in the process.

Another aspect of the residual cannabinoids oil is that the oil typically acquires/takes on flavor from the infused consumable. As indicated above, the process used to infuse bacon with cannabinoids produces a residual cannabinoids infused, bacon flavored oil and bacon grease mixture. The processes used to infuse other consumables likewise results in a flavored, cannabinoids infused oil. For example, the residual oil from the process used to produce cannabinoids infused garlic will have a garlic flavor; residual oil from cannabinoids infused fruit will have a fruit flavor, residual oil from cannabinoids infused with coffee will have a coffee flavor, and so on. The flavored, cannabinoid infused oils can be used to impart flavors and cannabinoids to other foods in several ways, such as, but not limited to, by directly using the infused oil on food, as a cooking oil, in the infusion methods disclosed herein, and so forth.

EXAMPLE X

Ice Cream, Jams, and Jellies with Infused Fruit

As detailed above, cannabinoids infused fresh and dehydrated fruits can be produced by methods disclosed herein. Such cannabinoids infused fruits can in turn be used in ice cream, jams, and jellies to produce cannabinoids infused, flavored ice cream, jams and jellies. For example, cannabinoids infused fresh fruit can be used to make a slurry that in turn can be used in making ice cream, jams, or jellies, resulting in cannabinoids infused, flavored ice cream, jams, or jellies. The cannabinoid content of such products can be increased by adding other cannabinoids infused consumables, such as cannabinoids infused nuts and/or chocolate.

EXAMPLE XI

Caramel Sauce Containing Infused Cannabinoids

As detailed above, cannabinoids infused food grade oils can be produced by the methods disclosed herein. Such oils can in turn be added to caramel sauce to produce a cannabinoids containing caramel sauce. A cannabinoids containing caramel sauce can be used in the production of ice cream to add cannabinoids into the ice cream. Alternatively, a cannabinoids containing caramel sauce can be used as a topping, a flavoring agent/ingredient for other foods, and so forth. In this regard, cannabinoids containing caramel sauce can be used to add both flavor and cannabinoids to a variety of consumables.

EXAMPLE XII

Cannabinoids Infused Baked Goods

As detailed above, cannabinoids infused food grade oils can be produced by the methods disclosed herein. Such infused oils can in turn be used to make various baked goods, such as cookies, brownies, quick breads, and so forth. In this regard, cannabinoids infused oils can be added as a base ingredient for baked goods, such as the food grade oil in baked goods or in combination with other base ingredients, such as butter. In one exemplary embodiment, a ratio of 75% cannabinoids infused oil to 25% butter is used as a base ingredient in making cookies, brownies, and other baked goods.

EXAMPLE XIII

Cannabinoids Infused Freeze Dried Consumables

As detailed above, cannabinoids infused food grade oils can be produced by the methods disclosed herein. Such infused oils can in turn be used to make a wide variety of various cannabinoids infused consumables, such as infused raw fruit, ice cream, and so forth. A wide variety of cannabinoids infused consumables can in turn be treated by the process of lyophilization, commonly known as freeze-drying, to turn the cannabinoids infused consumables into another form of consumable. Lyophilization typically removes 98% of the original water content, typically resulting in a crunchy and/or creamy consumable. Accordingly, the methods described herein can be applied to produce cannabinoids infused consumables that in turn are freeze-dried to produce freeze-dried cannabinoids infused consumables. The freeze-drying process allows foods such as infused fruit to retain both its cannabinoids and its nutrition.

EXAMPLE XV

Pressure Cooked Cannabinoids Infused Consumables

As detailed above, cannabinoids infused food grade oils can be produced by the methods disclosed herein. Such infused oils can in turn be used to make a wide variety of various cannabinoids infused consumables by methods that include heating and freezing steps to infuse the consumables with cannabinoids, as described above. In an exemplary embodiment, the heating steps may be carried out under pressure, such as in a pressure cooker. In this regard, the levels of infused cannabinoids in an infused consumable produced with pressure cooking can be greater than the relative levels obtained without pressure cooking. Accordingly, pressure cooking or similar pressurized heating can be used to produce consumables that have even higher levels of infused cannabinoids when compared to the infused consumables produced by the methods disclosed herein.

EXAMPLE XVI

Cannabinoids Infused Non-Consumable Products

As detailed above, cannabinoids infused oils can be produced by the methods disclosed herein. Such infused oils can in turn be used to make a wide variety of various cannabinoids infused non-consumable products. For example, many hair care products such as, but not limited to, hair shampoo, hair conditioner, mousse, balm, pomades and so forth may contain or be enhanced with various oils. Cannabinoids, and in particular CBD-A, may provide enhanced or improved properties to such hair care products. For example, CBD-A has been indicated as having hair restorative properties. Accordingly, the methods used to produce cannabinoid infused oils as described above can be used to produce hair care products enriched with cannabinoids and in particular, CBD-A. To obtain cannabinoids infused oil that has a high level of CBD-A, oils are prepared followed the general process described above in FIG. 2 (minus step 114) and steps 102-112, with the major exception that the oil is not heated to 250° F. (step 114), since that step decarboxylates CBD-A to CBD. Accordingly, the general methodology used to produce cannabinoids infused oils can be used to produce such infused oils that have significant levels of CBD-A. Cannabinoids infused oils that contain high levels of CBD-A can in turn be used in products that benefit/are enriched by CBD-A. In particular, such products include hair care products.

The invention claimed is:

1. A method of infusing popcorn with at least one cannabinoid from *cannabis*, the method comprising:
    (A) providing *cannabis*;
    (B) freezing the *cannabis* for about 24 hours;
    (C) providing an orally ingestible oil at a temperature of 150° F.-200° F.;

(D) adding at least a portion of the *cannabis* of (B) to the oil of (C) to form a first *cannabis* and oil mixture;

(E) keeping the *cannabis* and oil mixture of (D) at a temperature of 150° F.-200° F. for 4-8 hours;

(F) freezing the *cannabis* and oil mixture of (E) and keeping it frozen for 8-12 hours;

(G) heating the *cannabis* and oil mixture of (F) to a temperature of 150° F.-200° F. for 2-4 hours;

(H) straining the *cannabis* and oil mixture of (G) to separate the oil from the *cannabis* to yield a cannabinoids infused orally ingestible oil;

(I) heating the cannabinoids infused oil of (H) to a temperature of 250° F. for 2 hours;

(J) adding popcorn kernels to the cannabinoids infused oil of (I) to form a popcorn kernels and infused oil mixture;

(K) heating the mixture of (J) to a temperature of 170° F.-185° F. for 8-9 hours;

(L) freezing the mixture of (K) for 6-12 hours;

(M) heating the mixture of (L) to a temperature of 170° F.-185° F. for 8-9 hours;

(N) freezing the mixture of (M) for 6-12 hours;

(O) heating the mixture of (N) to a temperature of 100° F.-150° F. for 2-4 hours; and (P) straining the infused oil from the infused oil and popcorn kernels of (O) to yield cannabinoids infused popcorn and wherein the orally ingestible oil is a food grade oil.

2. The method of claim 1, wherein the *cannabis* provided in (A) is selected from the group consisting of *Cannabis Sativa, Cannabis* Indica, and *Cannabis Ruderalis*.

3. The method of claim 1, wherein the oil provided in (C) is selected from the group consisting of coconut oil, medium chain triglycerides oil, vegetable oil, sunflower oil, olive oil, grape seed oil, butter, shortening, lard, and a combination thereof.

4. The method of claim 1, wherein the oil provided in (C) is coconut oil.

5. The method of claim 1, wherein the oil provided in (C) is medium chain triglycerides oil.

6. The method of claim 1, wherein oil provided in (C) is a mixture of coconut oil and medium chain triglycerides oil.

7. The method of claim 1, wherein the oil provided in (C) is a mixture of coconut oil and medium chain triglycerides oil at a ratio of 75% coconut oil to 25% medium chain triglycerides oil.

8. The method of claim 1, wherein the *cannabis* and oil are provided at a ratio of 1 pound of *cannabis* to 2 gallons of oil in (D).

9. The method of claim 1, wherein the *cannabis* and oil are provided at a ratio ranging from 10%, 20%, 30%, 40%, 50%, 75%, to 100% of 1 pound of *cannabis* to 2 gallons of oil in (D).

10. The method of claim 1, wherein the *cannabis* in (A) is buds of *cannabis*.

\* \* \* \* \*